United States Patent [19]

Ibsen et al.

[11] Patent Number: 5,767,170

[45] Date of Patent: Jun. 16, 1998

[54] DENTAL ADHESIVE COMPRISING AN UNSATURATED MONOMER, A COUPLING AGENT, A CROSSLINKER, LEACHABLE FLUORIDE AND A PHOTOINITIATOR

[75] Inventors: Robert L. Ibsen; Alan B. Matthews, both of Santa Maria; William R. Glace, Orcutt, all of Calif.

[73] Assignee: Den-Mat Corporation, Santa Maria, Calif.

[21] Appl. No.: 640,376

[22] Filed: Apr. 30, 1996

[51] Int. Cl.$^6$ .............. A61K 6/08; C08K 3/22; C08K 3/34; C08K 265/06

[52] U.S. Cl. .............. 522/81; 522/83; 522/103; 522/172; 522/173; 522/182; 522/908; 522/77; 523/177; 523/116

[58] Field of Search .............. 522/908, 71, 72, 522/79, 83, 103, 87, 77, 101, 182, 172, 173, 179; 523/117, 116

[56] References Cited

U.S. PATENT DOCUMENTS

| Re. 34,937 | 5/1995 | Ibsen et al. | |
|---|---|---|---|
| 4,659,751 | 4/1987 | Bowen | 523/116 |
| 4,674,980 | 6/1987 | Ibsen et al. | 433/228.1 |
| 4,738,722 | 4/1988 | Ibsen et al. | |
| 4,746,686 | 5/1988 | Waller | 522/14 |
| 4,964,911 | 10/1990 | Ibsen et al. | |
| 5,151,453 | 9/1992 | Ibsen et al. | |
| 5,304,586 | 4/1994 | Hammesfahr et al. | 522/83 |
| 5,334,625 | 8/1994 | Ibsen et al. | |
| 5,360,770 | 11/1994 | Chadwick | |
| 5,658,963 | 8/1997 | Qian et al. | 522/908 |

OTHER PUBLICATIONS

Material Safety Data Sheet—Bisco, Inc. One–Step, prepared Feb. 4, 1995.

"One–Step (TM) Forward, No Steps Back", by Mark A. Broussard, DDS, The Bisdent Globe, Vo. IV, Issue II, Spring 1995.

Product literature for One–Step (TM) Universal Dental Adhesive (undated).

Primary Examiner—Susan W. Berman
Attorney, Agent, or Firm—Dorsey & Whitney

[57] ABSTRACT

A single package adhesive for tooth bonding applications which comprises a bulk-water-free solvent-based homogeneous liquid containing:

1) An ethylenically unsaturated monomer that possesses a hygroscopic functional group that (a) is capable of chemically reacting with and through the ethylenic bond of the ethylenically unsaturated-functional monomer of 2) below, and (b) provides the capacity for chemical bonding to the surface to which the adhesive is applied.

2) A mixture of soft, medium and hard crosslinkers (cross linking agents) that are polyfunctional molecules where the functionality is complementary to the ethylenic unsaturation of the ethylenically-unsaturated-functional monomer of 1) above;

3) A measurable amount of a water/fluid leachable fluoride capable of being leached from the liquid in a metered amount, obtained from a fluoride source, such as a particulate siliceous fluoride containing filler suspended in the liquid, in which the fluoride therein is water leachable; and 4) a photoinitiator system, i.e., comprises a free radical photoinitiator that induces addition polymerization of an ethylenically unsaturated compound.

A method is described for using the adhesive in tooth bonding applications.

20 Claims, No Drawings

5,767,170

DENTAL ADHESIVE COMPRISING AN UNSATURATED MONOMER, A COUPLING AGENT, A CROSSLINKER, LEACHABLE FLUORIDE AND A PHOTOINITIATOR

BRIEF DESCRIPTION OF THE INVENTION

A single package adhesive for tooth bonding application comprising a bulk-water-free solvent-based homogeneous mixture of—

1) an ethylenically-unsaturated-functional monomer;

2) a coupling agent;

3) a crosslinker (cross linking agent);

4) a measurable amount of a water/fluid leachable fluoride capable of (a) being leached from the adhesive in a metered amount;

5) a photoinitiator;

6) optionally, a radiopaquing agent; and, optionally, a buffering agent.

Composite formation by adhesively interbonding with tooth components using this single package adhesive.

BACKGROUND TO THE INVENTION

GERISTORE®, TENURE®, and TENURE® QUIK ™, sold by Den-Mat Corporation, Santa Maria, Calif., are promoted for certain uses in dentistry. U.S. Pat. Nos. 4,738, 722, 5,334,625 and 5,151,453, incorporated herein by reference, describe GERISTORE™. GERISTORE™ is a small particle composite provided as a two-package adhesive system that contains fluoride, is radiopaque and hydrophilic. It has low-cure shrinkage, low coefficient of thermal expansion and high strength. It aggressively bonds by chemical coupling to dentin, enamel, composites used in dentistry, porcelain and metal, such as stainless steel. It is a paste/paste formulation that is easy to mix. It is capable of rapid cure by exposure to room temperature and for more rapid cure, by exposure to light. In addition, though it contains a fluoride, which could be toxic when ingested in large dosages, it is biocompatible and safe to use within a human or other animal when applied topically.

TENURE™ is a solvent based crosslinkable acrylic resin, provided as a solution/solution formulation, that is, a two-package system. Its composition is described in U.S. Pat. No. 4,964,911, patented Oct. 27, 1990, and more effectively disclosed in U.S. Pat. No. Re 34,937, patented May 16, 1995, the disclosure of which is incorporated by reference. It is not an ionomer and does not release fluoride ion. It is less hydrophilic than GERISTORE®. It too is a crosslinkable resin. It contains a volatile solvent (typically acetone), which readily evaporates. After evaporation, a film of the resin rapidly cures in situ. The film is light and/or heat cured to a thermoset condition. TENURE® bonds by chemical coupling to dentin, enamel, porcelain, metal and the composites typically used in dentistry. It has been recommended for use with GERISTORE® in chemically bonding GERISTORE™ to dentin or enamel.

TENURE® QUICK™ is a single package adhesive that is sold for the same applications as TENURE® and it is described in commonly assigned, patent application Ser. No. 08/515,185, filed Aug. 11, 1995, now abandoned, based on provisional application serial no. 60/000,804, filed Jul. 5, 1995.

Bisco Inc., 1500 W. Thordal Ave., Itasca, Ill., 60143, sells a "one-step" adhesive bonding acrylic resin system called "One-Step" that uses a single solution to form the adhesive resin film. It is cited to yield the following physical data in bonding to certain substrates:

| Substrates | SBS, MPa |
|---|---|
| Dentin (using etchant) | 27.3 (0.6) |
| Enamel (using etchant) | 30.4 (3.8) |
| Metals: | |
| Gold Alloy | 20.6 (5.0) |
| Rexillium III (Ni—Cr) | 25.5 (2.3) |
| Stainless Steel (316) | 29.2 (1.7) |
| Set Amalgam (TYTIN ® ) | 13.6 (1.5) |

There is a need for an adhesive composition with the properties of TENURE® that is designed to be used from a single package of ingredients.

THE INVENTION

This invention relates to a single package adhesive that is superior for tooth bonding applications which comprises a bulk-water-free solvent-based homogeneous liquid containing:

1) an ethylenically unsaturated-functional monomer that possesses a hygroscopic group that (a) is capable of chemically reacting with and through the ethylenic bond of the ethylenically unsaturated-functional monomer of 2) below, and (b) provides the capacity for chemical bonding to the surface to which the adhesive is applied. For example, the coupling agent may be an acrylic monomer that possesses acrylic unsaturation and contains a surface bonding group, such as one or more of the following groups:

| | |
|---|---|
| i) an alkylene polyether | vi) phosphinyl |
| ii) hydroxyl | vii) stannoyl |
| iii) quaternary ammonium | viii) amide |
| iv) tertiary amine | ix) alkylene amine |
| v) phosphoryl | x) alkoxysilyl |
| | xi) acyloxysilyl |

2) a mixture of soft, medium and hard crosslinkers (cross linking agents) that are polyfunctional molecules where the functionality is complementary to the ethylenic unsaturation of the ethylenically-unsaturated-functional monomer of 1) above;

3) a measurable amount of a water/fluid leachable fluoride capable of being leached from the liquid in a metered amount, obtained from a fluoride source, such as a particulate siliceous fluoride containing filler suspended in the liquid, in which the fluoride therein is water leachable; and 4) a photoinitiator system, i.e., comprises a free radical photoinitiator that induces addition polymerization of an ethylenically unsaturated compound.

An important facet of this invention is that the components of the formulation with the exception of the fluoride generating source, are sufficiently compatible with each other and the solvent of choice. This means that the combination of the ingredients used in making the invention form a stable homogeneous mixture, i. e., they form a stable solution that can be stored for an extended period of time. It is preferred in the practice of the invention that all of the components of the formulation with the exception of the fluoride source remain in solution at ambient conditions for months, without precipitation of any component. However, it is within the contemplation of this invention that one or more of the ingredients of the formulation may precipitate from the solution on standing. In those instances, the precipitate is a soft deposit that is readily redissolved by stirring.

The expression "water-free" is intended to cover the exclusion of intentionally-added water and the expression "relatively water-free" and "essentially anhydrous" are intended to encompass a product in which water is not intentionally added in bulk form. In either of these circumstances, water may be present as molecular water that is bound to any of the materials that are used in formulating the adhesive of the invention. The molecular water that is bound to any of the adhesive reactants of the adhesive of the invention can be readily removed by heating the reactant at moderate temperatures and conditions below that which either degrades or polymerizes the adhesive reactant, at a temperature at or above the boiling point of the reactant if the reactant is lower boiling than water. Such allows separation of the formulation component from bound or freely associated water. Whether such bound water is present or removed plays an insignificant role in the performance of the adhesive of the invention to the extent that the water does not co-react with any of the component making up the adhesive formulation, including the source for fluoride. In general, the adhesive is made with a solvent that is water soluble, and as a result, the small quantity of water in the adhesive is fully diluted by the solvent.

One distinction between this adhesive from other adhesives is the fact that it is an essentially anhydrous composition. It is anhydrous in that essentially no free water is added to the formulation. Any water in the formulation is bound water, i.e., water that is chemically bound to one of the ingredients in the formulation, as noted above. For example, the hydroxylated acrylates and/or the solvents may contain from about 0 to about 5 weight percent bound water, that is, water that is hydrogen bonded to the hydroxylated acrylate or the solvent structures. The overall adhesive formulation may be hygroscopic, and absorb water on standing. Such water is bound to the various adhesive formulation's chemicals' structures. For example, glycerol methacrylate, a preferred hydroxylated reactant, is hygroscopic and will absorb water on standing. However, the amounts of water in the formulation based on bound water will not, in any case, exceed about 2 weight percent of the weight of the adhesive formulation.

The inventive adhesive comprises a resin based on an ethylenically unsaturated-functional monomer that contains a hygroscopic group and exhibits hydrophilicity. Typical of such groups are hydroxyl, amide, amine, aliphatic ether, pyrrolidone, ureyl, and the like.

Another feature of the inventive adhesive is that it tenaciously bonds to surfaces onto which it is coated as well as securely ties up any inorganic filler that is included in its formulation. This is accomplished by virtue of the presence of fluoride and by the presence in the adhesive formulation of the invention of a plurality of crosslinking agents. The same formulation without the fluoride does not adhere as tenaciously and the same formulation without the plurality of crosslinking agents does not have the consistently high adhesion levels.

Chemical bonding means strong and weak bonding forces. Strong bonding forces, as used herein, refers to covalent, ionic, hydrogen bonding and complexation, and weak bonding forces, encompasses the other forms of bonding. Where weak bonding forces are employed, the extent of such bonding is such that the adhesion to the surface is of the nature of a stronger bonding force. For example, van der Waal forces are weak bonding forces. In the case of the invention, the amount of such forces existing between the adhesive and the surface will be sufficient to give the performance of a stronger bonding force.

Desirable crosslinking agents are materials, such as a molecule, that are functionally complementary to the ethylenically-unsaturated-functional monomer. Desirably, the crosslinking agent contains a functional group that is reactable with the ethylenic unsaturation. Preferably, the functional group is an acrylic ethylenic unsaturation. At another part of at least one of the crosslinking agent molecules is a surface bonding group that can impart one or more properties to the adhesive coating:

1) chemical bonding capabilities to the substrate surface to which the adhesive coating is applied; and/or 2) wetting agent properties in that it reduces the surface tension of the adhesive coating, causing the adhesive to spread across or penetrate more easily the surface of the substrate onto which the adhesive coating is applied.

In addition, the adhesive of the invention contains at least three different crosslinking agents. The crosslinking agent are a polyfunctional molecules where the functionality is complementary to the ethylenic unsaturation of the ethylenically-unsaturated-functional monomer. In one category of crosslinking agent, the functional groups are separated by an organic moiety that is wholly aliphatic, thus forming a soft crosslinker. In the second category of crosslinking agent, the functional groups are separated by an organic moiety that is partially aliphatic and partially aromatic, thus forming a medium crosslinker. In the third category of crosslinking agent, the functional groups are separated by an organic moiety that is essentially wholly aromatic, thus forming a hard crosslinker.

The soft crosslinker typically contains an organic moiety that separates the two ethylenically unsaturated groups that is an aliphatic group of up to 10 aliphatic carbon atoms. Preferably, the functional groups of the crosslinking agent are bonded to a central moiety that is aliphatic in nature. Illustrative of such flexible groups are the residues of ethylene glycol, diethylene glycol, propylene glycol, dipropylene glycol, and the like. The medium crosslinker typically contains an organic moiety that separates the two ethylenically unsaturated groups that is a mixture of aliphatic and aromatic groups. In the case of the medium crosslinker, the ethylenically unsaturated functional groups are bonded to a central group that has the flexibility of an alkane or an alkyl benzene containing compound, such as 2,2-bis(4-hydroxyphenyl)propane, 2,2,-bis(4-hydroxyphenyl)fluoroalkanes, and the like. Typically, the aromatic group of the medium crosslinker is a central moiety of the molecule. The hard crosslinker comprises an essentially rigid aromatic organic group that separates the two ethylenically unsaturated groups. Illustrative of such rigid groups are aromatic or aromatic rings such as benzene, biphenyl anthracyl, benzophenone, norbornyl, and the like. Such hard crosslinkers raise the $T_g$ of the cured coating. Such softer crosslinkers toughen the cured adhesive and can raise the $T_g$ of the cured coating, but not as high as other crosslinking agents that are classed as the medium and hard crosslinkers.

In order to cure the adhesive of the invention, its formulation is provided with a conventional free-radical photoinitiator. The invention also contemplates, as an optional feature, the use of free radical scavengers in the formulation.

A primary advantage of the invention is that the adhesive composition is an essentially anhydrous homogeneous liquid single-package system. This means that the adhesive composition is an essentially anhydrous solution that can be stored in and used from a single container, such as a glass or plastic bottle. Quite surprisingly, the adhesive of the invention yields a performance when used that is similar to the TENURE® two package system adhesive, described in U.S. Pat. No. Re 34,937 and superior to single package adhesives used in this art.

In particular, the invention relates to the improvement where the adhesive composition is an essentially anhydrous homogeneous liquid single-package system comprising:

1) an ethylenically-unsaturated-functional monomer, such as 2-hydroxyethyl-methacrylateand,1,2-dihydroxypropyl methacrylate, the like;

2) a soft crosslinking agent, such as triethylene glycol dimethacrylate, diethylene glycol dimethacrylate, tetraethylene glycol dimethacrylate, and the like;

3) a medium crosslinker such as 2,2-bis(4-methacryloxy 2-ethoxy-phenyl) propane;

4) a hard crosslinker that is characterized by one or more compounds of the following formulae:

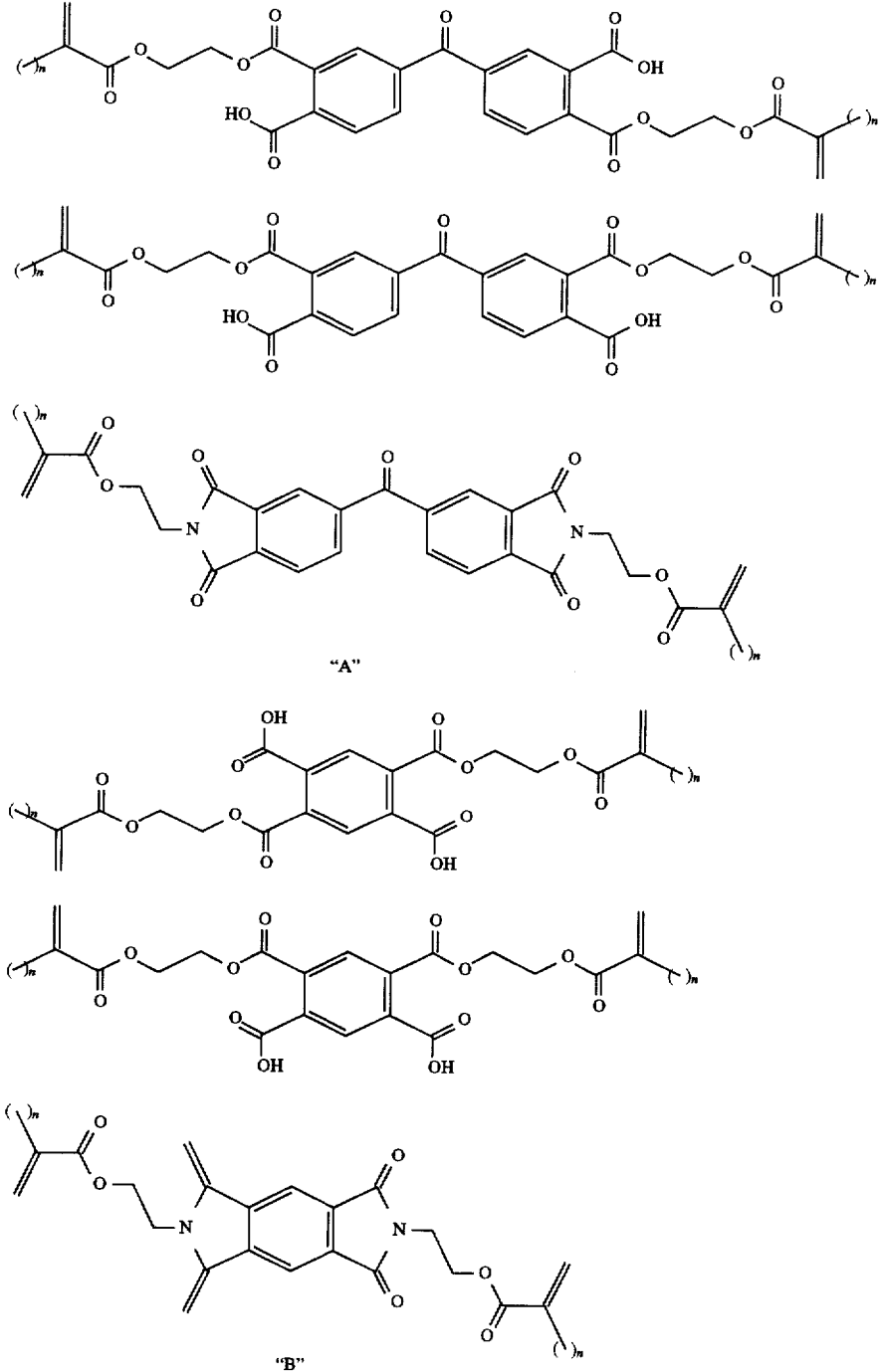

-continued
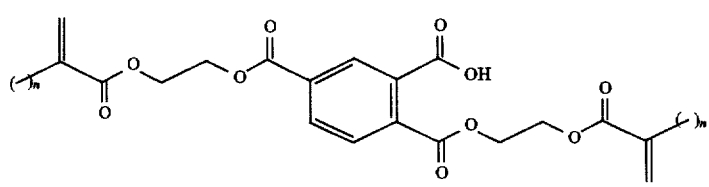
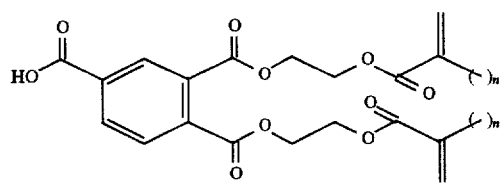
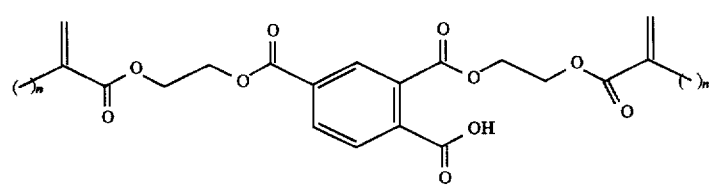
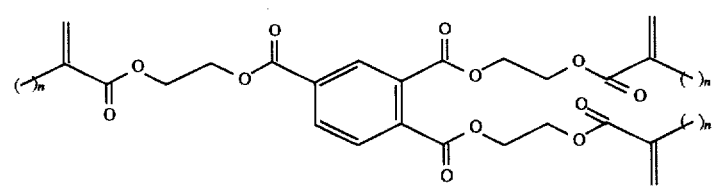
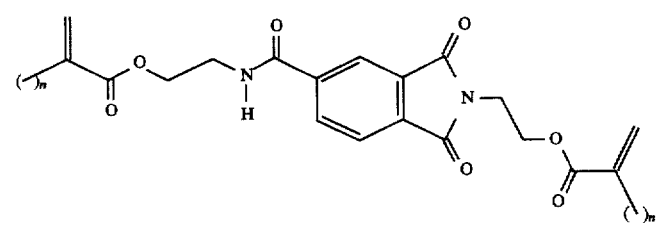
"C"
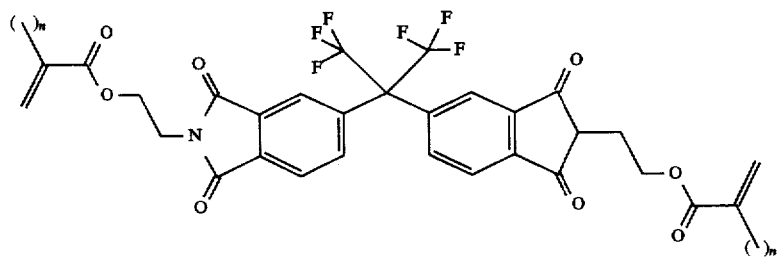
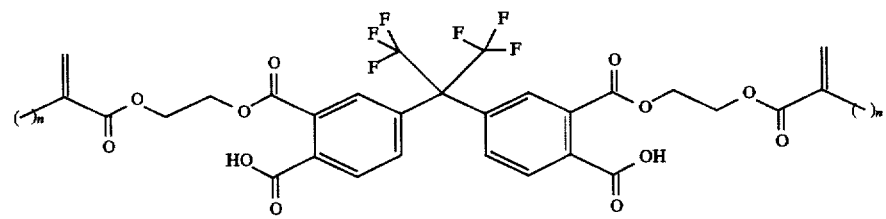

-continued

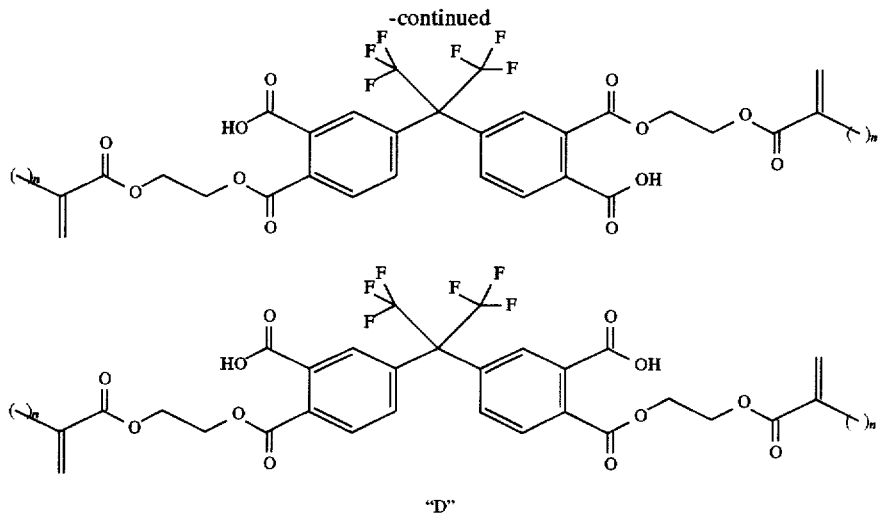

"D"

wherein n is 0 or 1; preferably mixture of such crosslinker; and

4) A fluoride source for water leachable fluoride, such as fluoride component that is present in the adhesive as a component of a non-resinous component of the formulation. The fluoride component may be, but need not be soluble in the resin component of the adhesive. In the preferred practice of the invention, the fluoride component in the adhesive formulation will dissolve in water and to the extent the water is removed from the fluoride source, fluoride is carried with it. As noted above, the particularly desirable form of the fluoride component, is an inorganic fluoride in which the fluoride is present, e.g., in the form of an fluorosilicate structure or an alumina fluoride structure. The fluoride source of U.S. Pat. No. 5,360,770 is a glass composition in which the fluoride content is derived from an alkaline earth metal fluoride such as calcium fluoride, barium fluoride and strontium fluoride. A most preferred fluoride source is described in U.S. Pat. No. 5,360,770 which is incorporated herein by reference, particularly the examples and illustration of the patent that show how to make the fluoride source. The fluoride is leachable from the adhesive over a three to four month period.

5) a photoinitiator; and 6) a water soluble organic solvent such as acetone.

In the preferred embodiment of the invention, the adhesive formulation is an essentially anhydrous solution comprising:

a) 2-Hydroxyethylmethacrylate or Glycidyl methacrylate;

b) Triethylene glycol dimethacrylate;

c) Ethoxylated bisphenol A dimethacrylate, i. e., 2,2-bis (4-methacryloxy 2-ethoxy-phenyl) propane;

d) The dimethacrylate of pyromellitic dianhydride;

e) A fluorosilicate structure or an alumina fluoride structure suspended therein;

f) A photoinitiator such as ethyl 4-dimethylamino benzoate and camphoquinone (i.e., 2,3-bornanedione); and g) Acetone.

The use of the adhesive composition of the invention to form a composite structure, involves, in one preferred embodiment, the steps of—

(a) optionally, contacting the adherend surface with an aqueous solution comprising at least one strong acid or acidic salt in order to condition the surface, followed by rinsing and drying the surface;

(b) coat the surface with the essentially anhydrous adhesive of the invention;

(c) cure the adhesive with light;

(d) apply a compositing material to the coating; and (e) cure the compositing material in contact with the coating.

The adhesives of the invention are suitable for a variety of dental application, ranging from restorations to the teeth, bonding to and with enamel, dentin, porcelain, plastics and metal prosthesis (precious and non-precious metals), and the like.

DETAIL DESCRIPTION OF THE INVENTION

The adhesive coating based on the adhesive formulation of the invention is typically a crosslinked light set resin that contains hygroscopic groups that attract water to the coating. When the crosslinking is not too extensive, the adhesive coating can absorb enough water that it can swell. The amount of water that the adhesive can absorb can be as high as 25 weight percent. However, the degree of crosslinking of the adhesive coating is typically high enough that water absorption will not exceed about 5 weight percent. The backbone of the polymer providing the hygroscopic groups of the resin phase of the adhesive coating is typically aliphatic and may contain groups therein that enhance the hydrophilicity of the resin phase. The adhesive coating's resin is typically the in situ reaction product of one or more of a polymerizable ethylenically unsaturated organic monomer containing groups that are attractive to water. Thus the components of the adhesive formulation may be—

An ethylenically unsaturated-functional monomer that contains a hygroscopic group. Typical of such groups are hydroxyl, amide, amine, aliphatic ether, amine, hydroxyalkyl amine, hydroxyalkyl amide, pyrrolidone, ureyl, and the like. Illustrative of such monomers are the following:

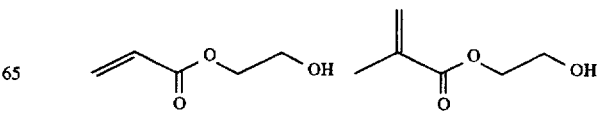

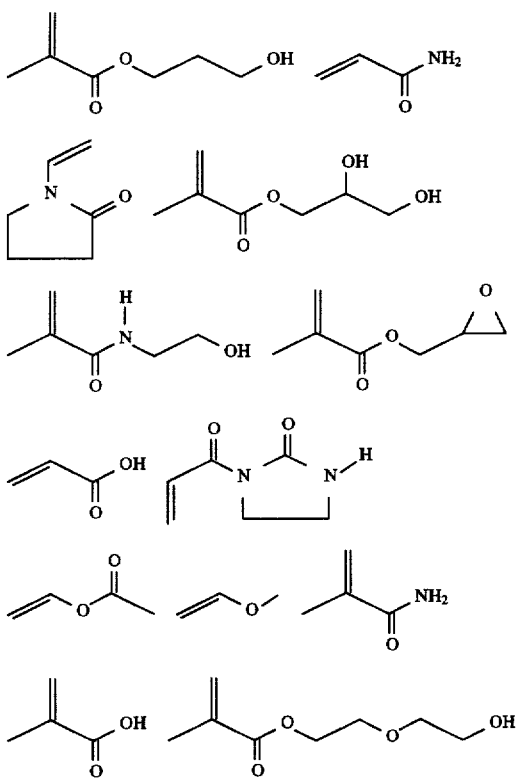

A particularly desirable ethylenically unsaturated-functional monomer is an acrylic-monomer having the following structure:

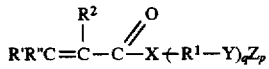

wherein R' and R", individually, are hydrogen, alkyl of 1 to about 4 carbon atoms, monocyclic aryl, such as phenyl, alkyl phenyl where the alkyl is 1 to about 3 carbon atoms, cyclohexyl, and the like; $R^2$ is hydrogen, alkyl of 1 to about 3 carbon atoms, and the like; X is O, S and N—$R^3$, where $R^3$ is hydrogen, alkyl of 1 to about 4 carbon atoms, —$R^1$—Y, and the like; $R^1$ is a divalent radical connecting Y to X, and may be one of the following:

—CH$_2$—  —CH$_2$CHR$^4$—  —CH$_2$CH$_2$CH$_2$—

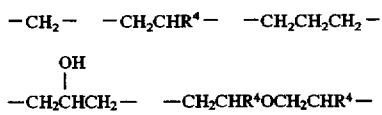

wherein each $R^4$ is hydrogen or alkyl of 1 to about 3 carbon atoms; and Y is OH, NR$^5$, SH, OR$^6$, where $R^5$ is hydrogen, methylol, methylol methyl ether, $R^6$ is alkyl of 1 to about 3 carbon atoms provided that $R^1$ is —CH$_2$—, and the like; q is 0 or 1 and p is 0 or 1, and p is 0 when q is 1 and 1 when q is 0; and Z is hydrogen.

A particularly desirable thermosetting adhesive is based on 2-hydroxyethyl methylmethacrylate ("HEMA"), 2-hydroxyethyl acrylate, 2,3-dihydroxypropyl methacrylate, acrylamide, methacrylamide, hydroxyalkyl acrylamide, hydroxyalkyl methacrylamide, and the like materials, and includes generally, acrylic monomer that possesses acrylic unsaturation and contains a surface bonding group possessing one or more of the following groups:

| | |
|---|---|
| 1) an alkylene polyether; | 7) alkoxysilyl |
| 2) hydroxyl | 8) phosphoryl |
| 3) carboxyl | 9) phosphinyl |
| 4) carboxylic acid salt | 10) stannoyl |
| 5) quaternary ammonium | 11) amide |
| 6) tertiary amine | 12) alkylene amine |
| | 13) acyloxysilyl |

These coupling agents interreact with the polymerization of the aforementioned diethylenically unsaturated-functional monomer that serve to crosslink the adhesive.

A number of acrylic adhesive resins rely on polyacrylyl substituted monomers to crosslink and chain extend the polymer that comes into existence on polymerization in the presence of an polymerization initiator. For example, the pure forms of HEMA typically contain small amounts of ethylene glycol dimethacrylate which will crosslink a polymer based on HEMA. The degree of crosslink may be so minuscule as to have little effect on the ultimate properties of the polymer. Crosslinking agents are frequently added to HEMA based resins to impart a particular quality of crosslinking and toughness to the cured resin. For example, diethylene or triethylene glycol dimethacrylate can otherwise lower the crosslink density of the resin which may impart toughness to the resulting cured polymer. Those types of crosslinkers would be considered a soft crosslinker, as defined above. However, in the practice of this invention, it is desired to use three type of crosslinkers, one that is hard, one that is medium hard, and one that is soft. In this respect, one may include the above crosslinker, in its normal impurity concentrations, as part of the soft crosslinker, but in the preferred embodiment, it is desirable to employ hard, medium and soft crosslinkers that contain at least two acrylyl groups bonded to aromatic containing moiety(ies) and two acrylyl groups bonded to an aliphatic moiety. A desirable hard crosslinker is characterized by the following formulae:

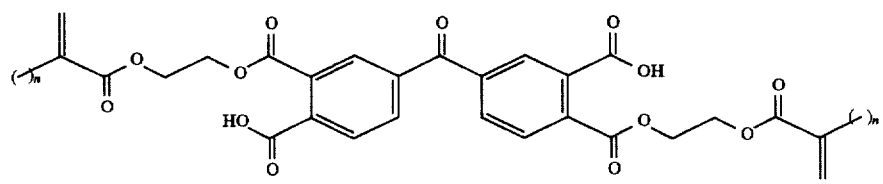

-continued
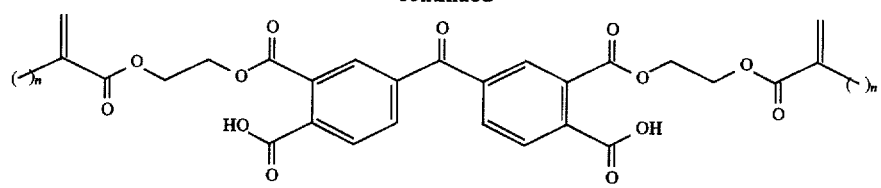
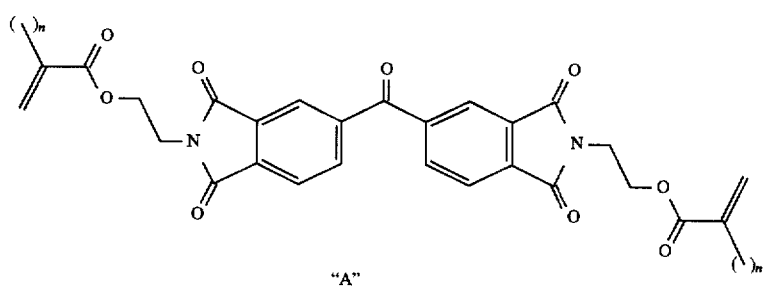
"A"
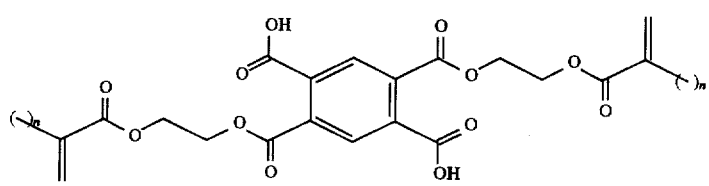
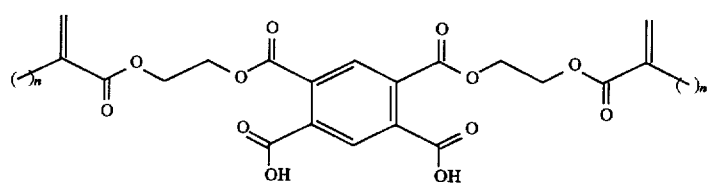
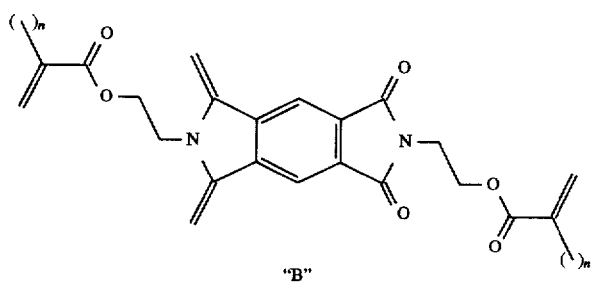
"B"
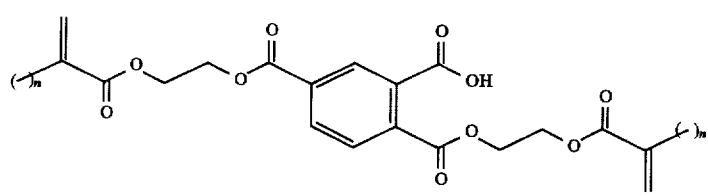
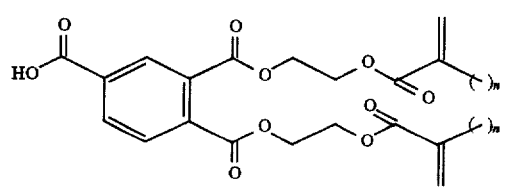

-continued
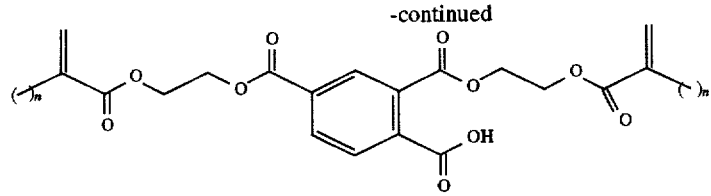
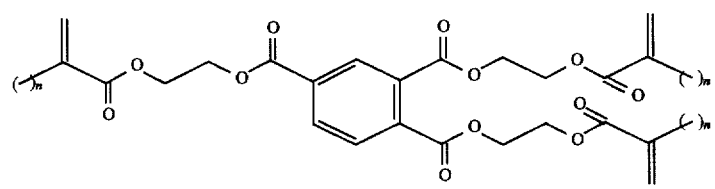
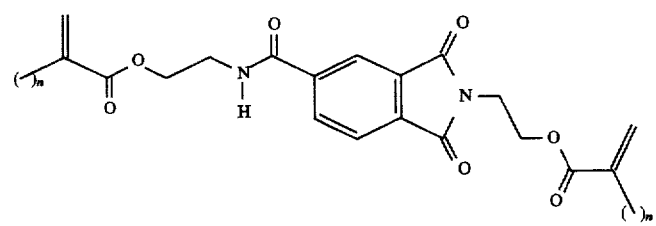
"C"
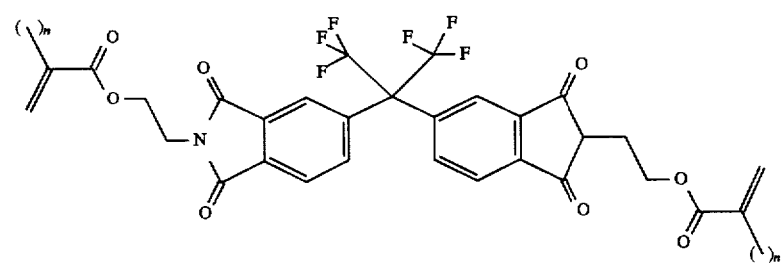
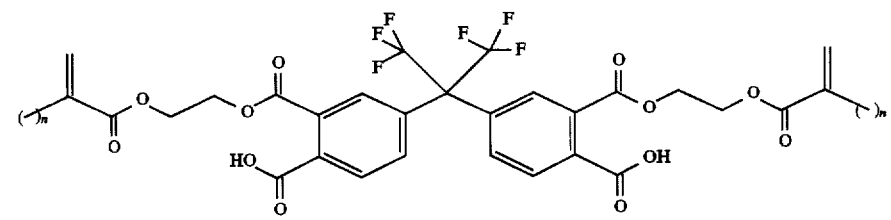
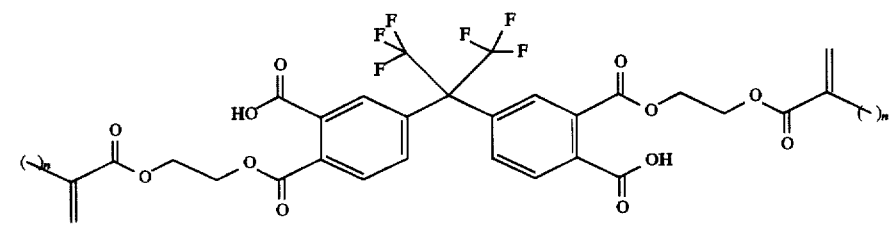
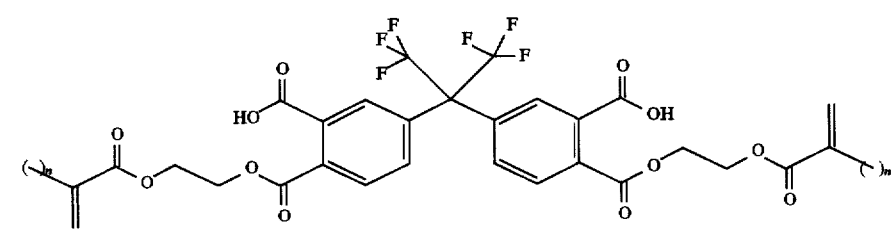
"D"

wherein n is 0 or 1. The preferred hard crosslinking agent is one of (i) the esters or imides of pyromellitic acid dianhydride and 2-hydroxyethyl methacrylate or 2-aminoethyl methacrylate, or the corresponding acrylates, as illustrated in group B above, (ii) the ester or imides of 3,3',4,4'-benzophenonetetracarboxylic dianhydride and 2-hydroxyethylmethacrylate or 2-aminoethyl methacrylate, or the corresponding acrylates, as illustrated in group A above, (iii) the esters and imide/amides of 4-trimellitic acid anhydride and 2-hydroxyethylmethacrylate or 2-aminoethyl methacrylate, or the corresponding acrylates, as illustrated in group C above, (iv) the ester or imides of 2,2-bis(3,4,-dianhydridophenyl)-1,1,1,3,3,3-hexafluoropropane and 2-hydroxyethyl methacrylate or 2-aminoethyl methacrylate, or the corresponding acrylates, as illustrated in group D above, and (v) other compounds containing at least one group or moiety capable of free radical polymerization and at least one aromatic ring or moiety containing electron-withdrawing substituents that do not interfere with free radical polymerization. The medium crosslinker is typically an diacrylic or dimethacrylic ester or ether of the ethylene oxide adduct of bisphenol A. The soft crosslinkers are the other glycol dimethacrylates and diacrylates mentioned herein. Preferred medium crosslinkers are ethoxylated bisphenol A dimethacrylate and the adduct of glycidylmethacrylate and bisphenol A.

The fluoride component is present in the adhesive as a component of a non-resinous component of the formulation. The fluoride component may be, but need not be soluble in the resin component of the primary coating. In the preferred practice of the invention, the fluoride component in the adhesive will dissolve in water and to the extent the water is removed from the fluoride source, fluoride is carried with it. As noted above, the particularly desirable form of the fluoride component, is an inorganic fluoride in which the fluoride is present, e.g., in the form of an fluorosilicate structure or an alumina fluoride structure. The fluoride source of the patent is a glass composition in which the fluoride content is derived from an alkaline earth metal fluoride such as calcium fluoride, barium fluoride and strontium fluoride. A most preferred fluoride source is described in U.S. Pat. No. 5,360,770 which is incorporated herein by reference, particularly the examples and illustration of the patent that show how to make the fluoride source. As noted above, the adhesive is optionally provided with a leachable fluoride component. The fluoride is leachable from the coating over a three to four month period. This means that after many days and even months, the coating should be able to release small measured amounts of fluoride into the wound area. The longevity of the fluoride in the coating and the ability to meter it from the coating are dependent on a number of factors, such as:

the concentration of fluoride in the coating;

the nature of the chemical bond of the fluoride within the coating composition;

the level of hygroscopicity of the coating;

if the fluoride is part of a solid, the degree of particulateness of the solid, coupled with the rate at which fluoride can be leached from the solid;

if the fluoride is part of a liquid molecule, the rate at which the fluoride is cleaved from the molecule to form a leachable fluoride; and if the fluoride is part of a polymer, the rate at which fluoride in the polymer can be solubilized and leached from the polymer.

A particularly desirable form of the fluoride component, is an inorganic fluoride in which the fluoride is present, e.g., in the form of an fluorosilicate structure or an alumina fluoride structure. Illustrative of such fluoride structures are fluorite (or fluorspar), $CaF_2$, $BaF_2$, $SrF_2$, cryolite, $Na_3AlF_6$, and fluorapatite, $3Ca_3(PO_4)_2Ca(F,Cl)_2$. A preferred fluoride source is described in U.S. Pat. No. 5,360,770. The fluoride source of the patent is a glass composition in which the fluoride content is derived from an alkaline earth metal fluoride such as calcium fluoride, barium fluoride and strontium fluoride. A particularly preferred glass composition that provides fluoride is the following:

TABLE 1

| Component | Mole % | Component | Mole % |
|---|---|---|---|
| $SiO_2$ | 17.6–21.6 | $P_2O_5$ | 0.8–3.5 |
| $Al_2O_3$ | 9.0–11.0 | $Na_2O$ | 0.5–3.0 |
| MO | 7.9–19.7 | F | 42.2–56.1 | in which M is an alkaline earth metal and MO is barium oxide and barium oxide binary and ternary mixtures with other alkaline earth metal oxides, such as BaO, BaO—CaO, BaO—SrO and CaO—BaO—SrO. Such preferred source of fluoride not only provides long term fluoride release from the adhesive but it also provides an essentially uniform release of fluoride over that period of time. FIGS. 1 and 2 illustrate the long term fluoride leachability of this fluoride source. FIG. 1 illustrates the release of fluoride by placing the aforementioned barium oxide based glass in water and determining the release of fluoride over an extended period of time. As can be seen, the fluoride release follows a straight line showing uniform release over 550 days, about 1½ years. FIG. 2 shows area plots of ingredients in order to optimize the glass formulation for maximizing the fluoride release over an extended period, e.g., 1½ years.

Also included in the formulation, as an optional ingredient, is a photoinitiator. According to one aspect this invention, the light-initiated curing of a polymerizable matrix material involves photosensitization of light-sensitive compounds by ultraviolet or visible light, which, in turn, initiates polymerization of the matrix material. The photoinitiator to be used in this invention comprises a combination of a photosensitive ketone and a tertiary amine. Typical photosensitive ketones include benzophenone, acetophenone, thioxanthen-9-one, 9-fluorenone, anthraquinone, 4'-methoxyacetophenone, diethoxyacetophenone, biacetyl, 2,3-pentadione, benzyl, 4,4'-methoxybenzil, 4,4'-oxidibenzil, and 2,3-bornadione (dl camphroquinone). Typical tertiary amines include ethyl-4-dimethyl amino benzoate, ethyl-2-dimethyl amino benzoate, 4,4'-bis(dimethylamino) benzophenone, N-methyldiethanolamine, and dimethylaminobenzaldehyde. A preferred combination of the photoinitiators is 2,3-bornanedione with ethyl-4-dimethyl amino benzoate. Other suitable initiator are illustrated in U.S. Pat. No. 4,674,980 to Ibsen, et al., the disclosure of which is incorporated by reference. Alternatively, any known photosensitizing system which can function effectively in a one package composition when exposed to light may substitute for the above-named compounds or combinations. The amount of the photoinitiator should be sufficient to initiate polymerization in a selected resin and complete it in depth within about half a minute when the filler-resin composition is exposed to a visible-light output of at least 5,000 foot candles. In addition, any known free-radical scavenger (anti-oxidants) such as butylated hydroxytoluene can be used to scavenge small amounts of free radicals generated during extended shelf storage.

The polymerization system of the adhesive may depend on effecting cure with either the photoinitiator or by use of a thermal initiator, which is a typical thermal curing agent known in the art. Illustrative of these are benzoyl peroxide, dicumyl peroxide, ditertiary butyl peroxide, tertiary butyl hydroperoxide, cumyl hydroperoxide, or other suitable peroxides may initiate polymerization of the polymerizable ethylenically unsaturated components of the primary coating. Addition of such thermal initiators is desirable to insure complete polymerization. Even when light alone does not cure the matrix material, the peroxide initiates curing of the uncured material thermally upon standing. Benzoyl peroxide may be used together with 2-hydroxyethyl-p-toluidine.

The adhesive may contain pigments such as iron oxide or titanium oxide and a color stabilizing agent such as 2,2-hydroxy-5-tert. octyl phenylbenzotriazole.

In formulating the primary coating, the selection of the ingredients in formulating the coating is narrowly critical. Illustrative of such a formulation are the adhesive compositions as set forth in Table 2.

TABLE 2

| Ingredients | Percentage by Weight | Preferred Composition % by weight |
|---|---|---|
| Glass, fluoride source (e.g., the Calcium fluoroaluminosilicate of Table 2, supra. | 5–20 | 9.0909 |
| Ethylenically unsaturated monomer, e.g., 2-hydroxyethyl methacrylate | 3–15 | 8.9533 |
| Soft Crosslinker, e.g., Triethylene glycol dimethacrylate | 2–10 | 8.9533 |
| Medium Crosslinker, e.g., Ethoxylated bisphenol A dimethacrylate | 3–15 | 8.9533 |
| Hard Crosslinker, e.g., PMDM | 2–20 | 6.9533 |
| Acetone | 20–65 | 52.2779 |
| 2,3-bornanedione | 0.03–0.30 | 1.409 |
| Ethyl 4-dimethylaminobenzoate | 0.01–3 | 1.409 |

The preferred formulation was transferred to a small, black dropper bottle and tested as follows:

Bovine teeth are prepared to expose the dentin surface and are mounted in an acrylic mold to support them during preparation and testing. The teeth are etched with a dental etchant for 15 seconds containing 37% Phosphoric Acid and are rinsed and blotted dry. Three coats of the adhesive are applied, and gently air-dried to remove solvent and form a thin film. If the surface does not appear glossy, an additional coat is applied and air-dried. Once a glossy surface is achieved, the material is light-cured for 15 seconds, using a Marathon 2000 curing light. Next, a ring mold with an inner diameter of 3.21 mm and a depth of approximately 2 mm was positioned on the light-cured adhesive. This was filled with Dual-Cured Marathon Composite and light-cured for 45 seconds. The ring mold was carefully excised using a scalpel and the samples were placed into 37° C. water.

After 55 minutes, the samples were taken from the 37° C. water and tested on an Instron Model 1011 for shear bond strength using a 1000 # Load Cell with 0.2 in/min. crosshead speed on a knife edge tester set at the 100# Load Range. The adhesion obtained averaged 12.0 Mpa (x=3).

A typical restorative procedure for using the adhesive of the invention on dentin would encompass the following:

Prepare and clean dentin surface as is customary. Apply 37% phosphoric acid etchant to the tooth's surface and allow to sit for 15 seconds. Thoroughly rinse and gently blot or air-dry the area treated. Completely immerse a brush tip in the adhesive composition of the invention. Using a fully saturated brush tip each time, apply three consecutive coats of the adhesive to the phosphoric prepared tooth. Allow the adhesive to lie on the tooth for 15 seconds. Remove solvent from the adhesive by directing a gentle stream of dry, oil-free air from an air syringe onto the adhesive. The force of the air should be strong enough to extract the adhesive's solvent while not so forceful as to force the adhesive from the preparation. If the dentin surface is not glossy after drying, re-apply the adhesive and gently re-dry. Light-cure the adhesive for 15 seconds then apply another thin coat using adhesive remaining on the brush. Position and cure the restorative material as directed by the manufacturer.

Light having a wave length of about 480 ηM at an intensity of about 5000 foot-candles is preferred.

Typical surfaces for use of the adhesives of the invention include the following:

bovine bone tissue, dentin, stainless steel, enamel, porcelain, nonprecious (NP) metals titanium and hydroxyapatite (the principal bone salt, Ca5(PO4)3OH, which provides the compression strength of vertebrate bone).

We claim:

1. A single package adhesive for tooth applications which comprises a bulk-water-free solvent-based homogeneous liquid containing:

(1) an ethylenically unsaturated monomer that (a) is capable of chemically reacting with the ethylenic bonds of the multiethylenically unsaturated mixture of 2) below, (b) possesses a hygroscopic group, and (c) provides the capacity for chemical bonding to the surface to which the adhesive is applied;

(2) a mixture comprising at least one "soft" crosslinking agent that is wholly aliphatic, at least one "medium" crosslinking agent that is partially aliphatic and partially aromatic, and at least one "hard" crosslinking agent that is essentially wholly aromatic, wherein the soft, medium and hard crosslinking agents are multi-ethylenically unsaturated compounds;

(3) an amount of a water/fluid leachable fluoride capable of being leached from the liquid in a metered amount, obtained from a fluoride source suspended in the liquid; and (4) a photoinitiator system that induces addition polymerization of an ethylenically unsaturated compound.

2. The single package adhesive for tooth bonding applications of claim 1 wherein (1) is an acrylic monomer that comprises:

(i) acrylic unsaturation as defined by the following formula:

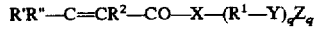

$$R'R''{-}C{=}CR^2{-}CO{-}X{-}(R^1{-}Y)_pZ_q$$

wherein R' and R", individually, are hydrogen, an alkyl of 1 to about 4 carbon atoms, a monocyclic aryl, or cyclohexyl; $R^2$ is hydrogen or an alkyl of 1 to about 3 carbon atoms; X is O, S or N—$R^3$ wherein $R^3$ is hydrogen, an alkyl of 1 to about 4 carbon atoms, or —$R^1$—Y; $R^1$ is a divalent radical connecting Y to X; Y is OH, $NR^5$, SH, or $OR^6$, wherein $R^5$ is hydrogen, methylol, or methylol methyl ether and $R^6$ is an alkyl of 1 to about 3 carbon atoms; q is 0 or 1 and p is 0 or 1, provided that p is 0 when q is 1 and p is 1 when q is 0; and Z is hydrogen; and (ii) a surface bonding group selected from the group consisting of alkylene polyether, hydroxyl, quartenary ammonium, tertiary amine, phosphoryl, phosphinyl, stannoyl, amide, alkylene amine, alkoxysilyl, and acyloxysilyl.

3. The single package adhesive for tooth bonding applications of claim 2 wherein the crosslinking agents contain acrylic ethylenic unsaturation.

4. The single package adhesive for tooth bonding applications of claim 3 wherein another part of at least one of the crosslinking agent molecules is a surface bonding group that can impart one or more of the properties of:

(1) chemical bonding capabilities to the substrate surface to which the adhesive coating is applied; and (2) wetting agent properties in that it reduces the surface tension of the adhesive coating, causing the adhesive to spread across or penetrate more easily the surface of the substrate onto which the adhesive coating is applied.

5. The single package adhesive for tooth bonding applications of claim 1 wherein the photoinitiator comprises a free radical photoinitiator.

6. The single package adhesive for tooth bonding applications of claim 1 wherein the solvent-based homogeneous liquid is stable.

7. The single package adhesive for tooth bonding applications of claim 6 wherein the solvent does not co-react with any of the components making up the adhesive formulation, including the source for fluoride.

8. The single package adhesive for tooth bonding applications of claim 7 wherein the solvent is water soluble.

9. The single package adhesive for tooth bonding applications of claim 1 wherein the soft crosslinker contains an organic moiety that separates the unsaturated groups that is an aliphatic group of up to 10 aliphatic carbon atoms.

10. The single package adhesive for tooth bonding applications of claim 1 wherein the aromatic portion in the medium crosslinker is a central moiety to the molecule.

11. The single package adhesive for tooth bonding applications of claim 1 wherein the aromatic groups in the hard crosslinker are selected from the group consisting of benzene, biphenyl, anthracyl, benzophenone, and norbornyl.

12. The single package adhesive for tooth bonding applications of claim 11 wherein the hard crosslinkers raise the $T_g$ of the cured adhesive coating.

13. The single package adhesive for tooth bonding applications of claim 1 wherein bulk-water-free solvent-based homogeneous liquid comprises:

1) an ethylenically-unsaturated monomer;

2) a soft crosslinking agent;

3) a medium crosslinker;

4) a hard crosslinker that is characterized by one or more compounds of the following formulae A, B, C and D, or a mixture thereof:

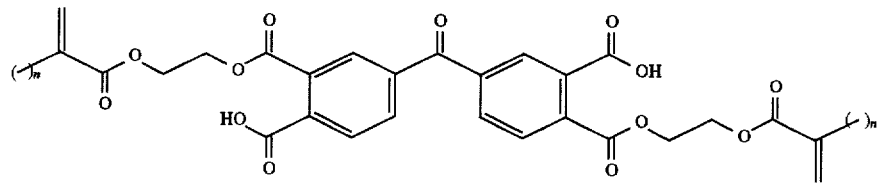

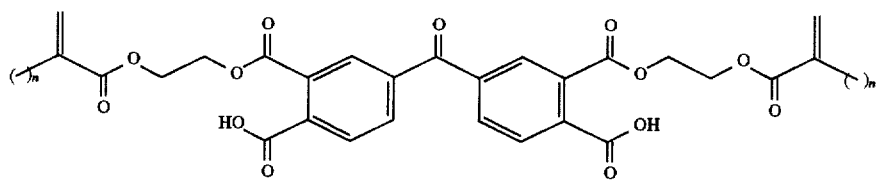

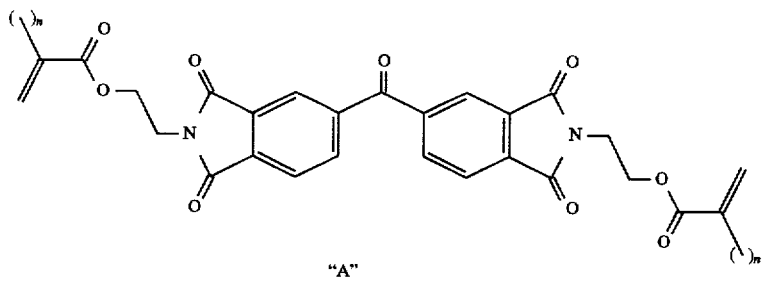

"A"

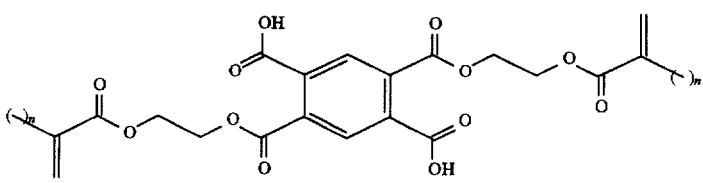

-continued
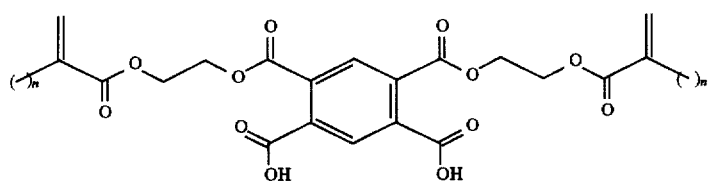
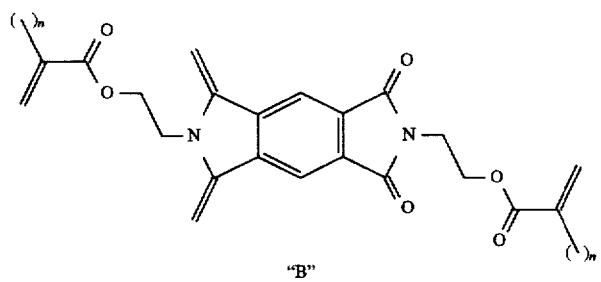
"B"
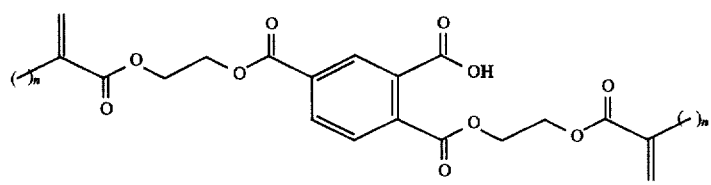
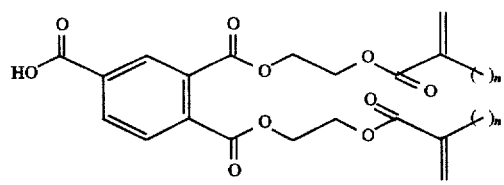
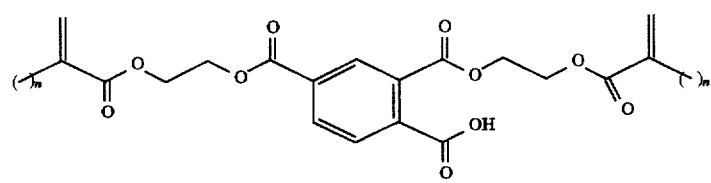
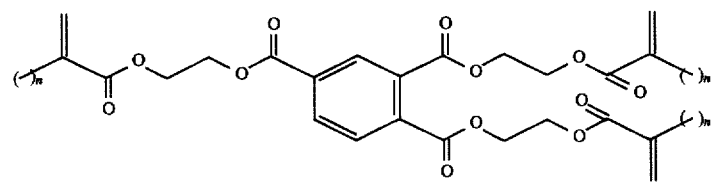
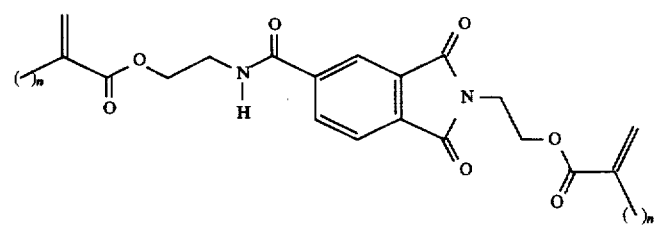
"C"

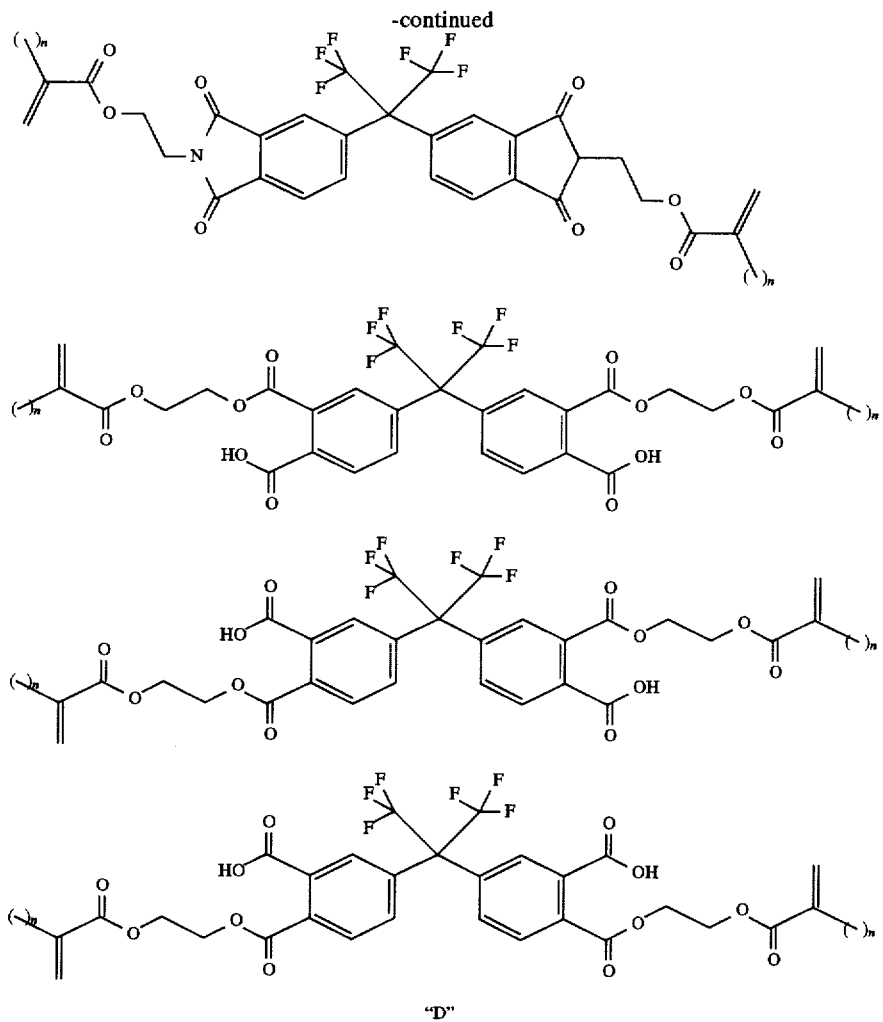

"D"

wherein n is 0 or 1; and 5) a fluoride source for water leachable fluoride, as fluoride component that is present in the liquid as a non-resin forming component of the formulation.

14. The single package adhesive for tooth bonding applications of claim 13 wherein the fluoride source is soluble in the liquid.

15. The single package adhesive for tooth bonding applications of claim 13 wherein the fluoride source is insoluble in the liquid.

16. The single package adhesive for tooth bonding applications of claim 13 wherein the fluoride source is an inorganic fluoride in which the fluoride is present in the form of an fluorosilicate structure or an alumina fluoride structure.

17. The single package adhesive for tooth bonding applications of claim 16 wherein the fluoride source is a glass composition in which the fluoride content is derived from an alkaline earth metal fluoride.

18. The single package adhesive for tooth bonding applications of claim 1 wherein the solvent is a water soluble organic solvent.

19. The single package adhesive for tooth bonding applications of claim 1 wherein the liquid comprises:

a) 2-Hydroxyethylmethacrylate or glycidyl methacrylate;
b) Triethylene glycol dimethacrylate;
c) Ethoxylated bisphenol A dimethacrylate;
d) a dimethacrylate of pyromellitic dianhydride;
e) a fluorosilicate structure or an alumina fluoride structure suspended therein;
f) a photoinitiator; and
g) Acetone.

20. The method of forming a composite structure, which comprises the steps of—

(a) contacting an adherent surface with an aqueous solution comprising at least one strong acid or acidic salt in order to condition the surface, followed by rinsing and drying the surface;
(b) coating the surface with the essentially anhydrous single package adhesive of claim 1;
(c) curing the adhesive with light;
(d) applying a compositing material to the coating; and
(e) curing the compositing material in contact with the coating.

* * * * *